United States Patent [19]

Lackey et al.

[11] Patent Number: 4,973,847
[45] Date of Patent: Nov. 27, 1990

[54] TOOTHBRUSH SANITIZING DEVICE

[75] Inventors: A. Wayne Lackey; Joseph F. Bello, both of Boca Raton, Fla.

[73] Assignee: Dentec Corporation, Boca Raton, Fla.

[21] Appl. No.: 389,263

[22] Filed: Aug. 3, 1989

[51] Int. Cl.⁵ ............................................. G01N 23/00
[52] U.S. Cl. .................................... 250/455.1; 422/24
[58] Field of Search ......................... 250/455.1; 422/24

[56] References Cited

U.S. PATENT DOCUMENTS

| | | |
|---|---|---|
| 2,280,431 | 4/1942 | Hart . |
| 2,336,224 | 12/1943 | Cohen . |
| 2,424,036 | 7/1947 | Jackel . |
| 2,554,156 | 5/1951 | Rosenthal . |
| 2,579,242 | 12/1951 | Pask . |
| 2,592,131 | 4/1952 | Farrar . |
| 3,100,842 | 8/1963 | Tellefsen . |
| 3,309,159 | 3/1967 | Le Sueur et al. . |
| 3,353,905 | 11/1967 | Ellis . |
| 3,748,094 | 7/1973 | Schiedell . |
| 3,820,251 | 6/1974 | Abernathy . |
| 3,881,868 | 5/1975 | Duke . |
| 3,954,407 | 5/1976 | Andary et al. . |
| 3,955,922 | 5/1976 | Moulthrop . |
| 4,088,445 | 5/1978 | Ellis . |
| 4,625,119 | 11/1986 | Murdock, III . |
| 4,698,206 | 10/1987 | Nevin . |
| 4,740,706 | 4/1988 | Murdock, III . |
| 4,803,364 | 2/1989 | Ritter . |
| 4,806,770 | 2/1989 | Hylton ............................ 250/455.1 |
| 4,816,648 | 3/1989 | Dusbabek ........................... 219/521 |
| 4,906,851 | 3/1990 | Beasley et al. .................. 250/455.1 |

Primary Examiner—Bruce C. Anderson
Attorney, Agent, or Firm—Roylance, Abrams, Berdo & Goodman

[57] ABSTRACT

Toothbrush sanitizing devices for home use. The devices include an outer housing, an inner housing, a cover and a sanitizing assembly. The inner housing is removably retained within the outer housing by an interference fit. The cover member is removably supported by the inner and/or outer housings such that the cover member and the outer housing form an enclosure, with the inner housing inside the enclosure. The inner housing has upwardly extending centering flanges for properly positioning the cover on the housings. The inner and outer housings form longitudinal slots to receive the handles of toothbrushes. The sanitizing assembly is attached to the inner housing and includes an ultra-violet lamp, an electronic printed circuit board, a microswitch and a switch member. The switch member is pivotably mounted in one of the centering flanges and is moved from the off to the on position when the cover is properly placed on the housings. The switch activates the microswitch which in turn activates the circuit board and lamp, such that the lamp is activated when the cover is positioned on the housings. However, the circuitry of the circuit board has a built-in time delay so that the ultra-violet lamp is not activated immediately after the switch member has been engaged, rather, the lamp is activated after the pre-determined time delay.

19 Claims, 3 Drawing Sheets

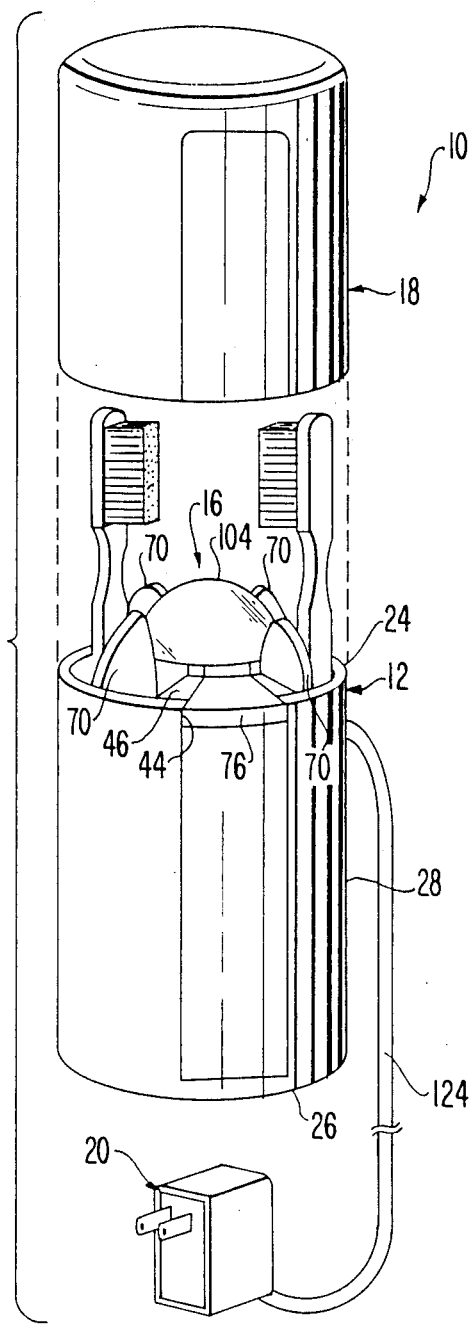
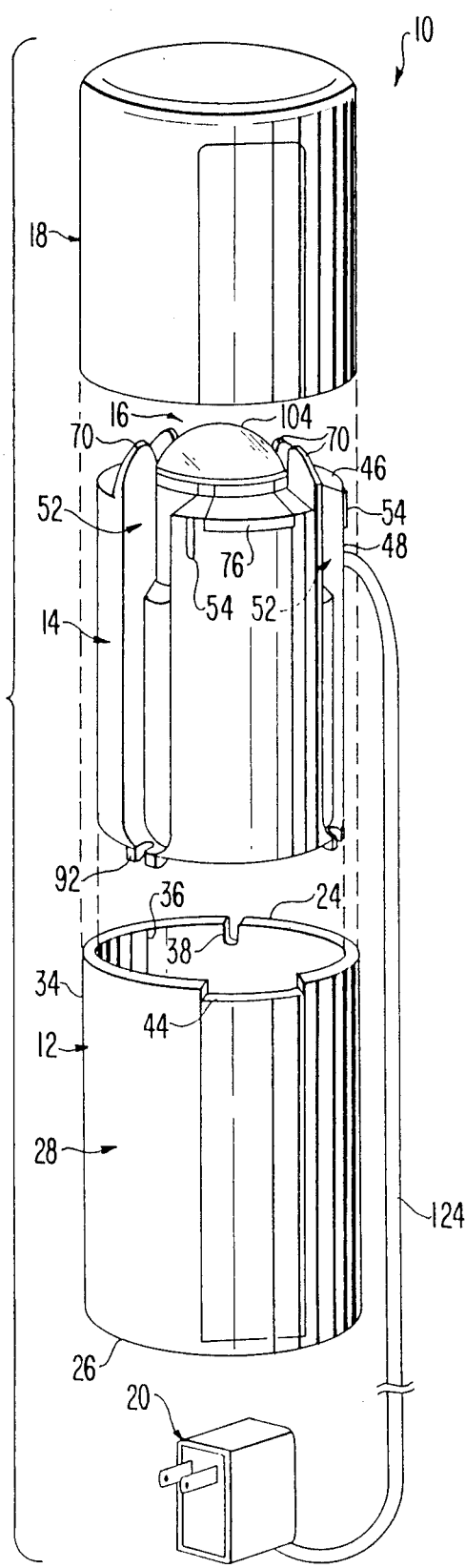

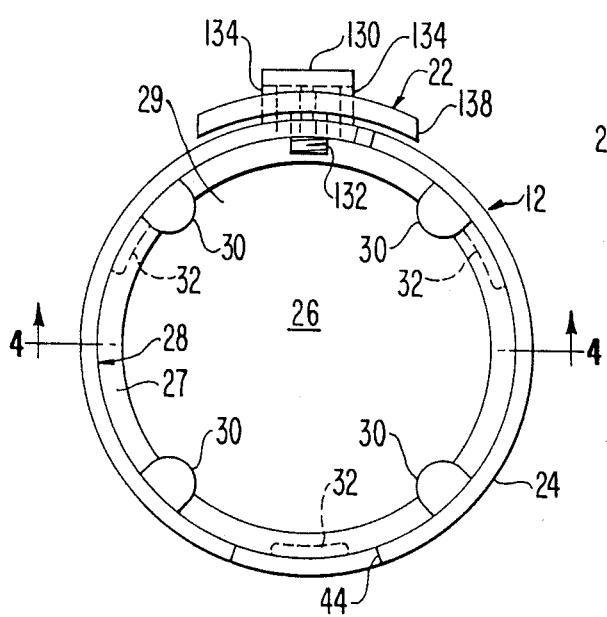
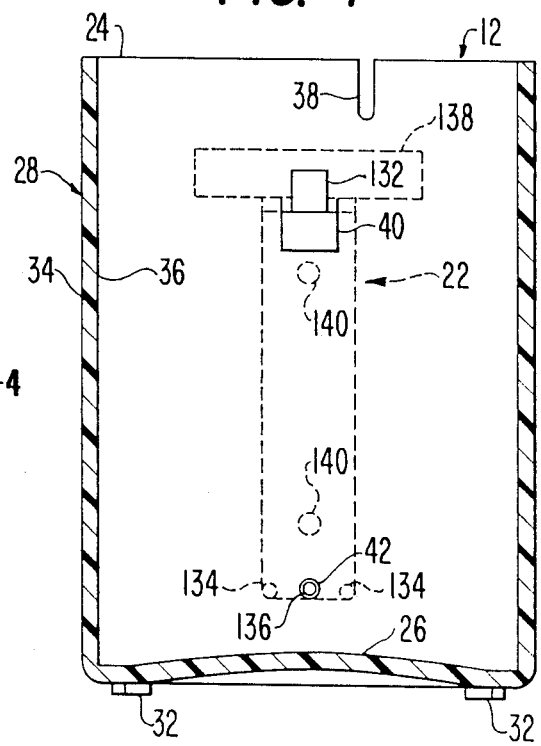
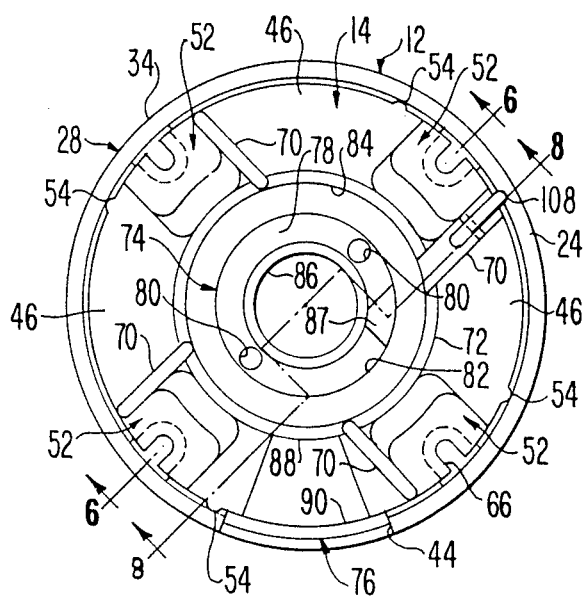
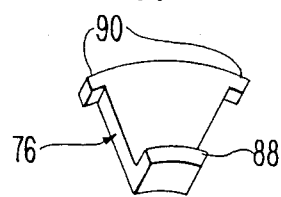
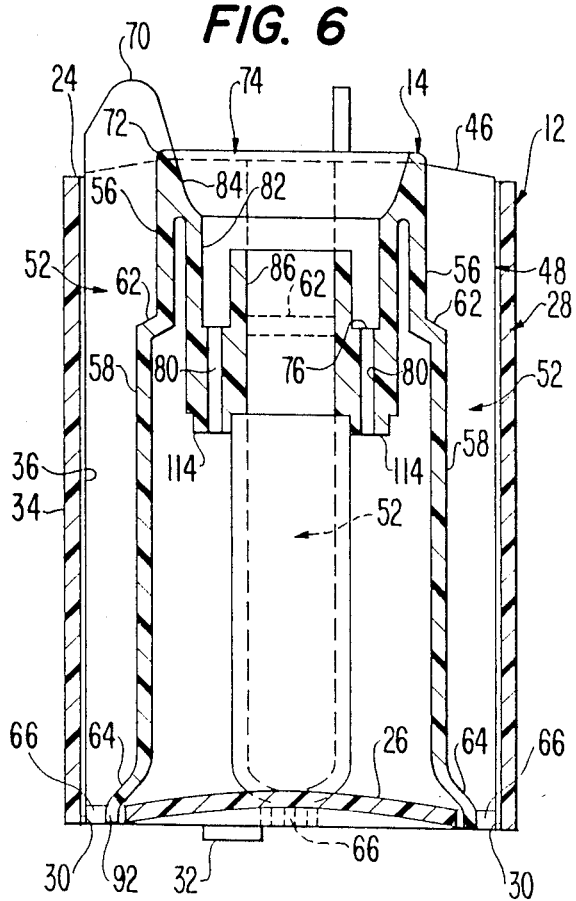

TOOTHBRUSH SANITIZING DEVICE

FIELD OF THE INVENTION

This invention relates to toothbrush sanitizing devices for use in homes to sanitize toothbrushes before and between uses. More specifically, this invention relates to such toothbrush sanitizers which employ ultra-violet light to sanitize toothbrushes and include, in a housing, an ultra-violet light assembly and structure to support toothbrushes such that the bristles of the toothbrushes are adjacent the light source of the light assembly.

BACKGROUND OF THE INVENTION

Studies have linked mouth infections and many other illnesses to the use of unsanitary toothbrushes. Furthermore, studies have indicated that germs carried on toothbrushes may extend the length of illnesses.

Specifically, studies have found germs on toothbrushes which are common in cases of pneumonia, stomach ulcers, strep throat, sinus disease, upset stomach and diarrhea. Individuals who have one of the above ailments may have a heavy germ build-up on their toothbrushes within twenty-four hours of first use of a new toothbrush. Even healthy individuals may have heavy germ build-up on their toothbrushes within thirty five days of use. Such germs may come from the user's own mouth and/or from the environment in which the toothbrush is kept between uses. Most toothbrushes are kept in bathrooms, which are often fertile environments for germs.

Moreover, a recent study revealed that 40% of all new, unused toothbrushes were germ-laden when removed from their packaging. No federal regulations or standards require sterilization or sanitization of toothbrushes before packaging and sale to customers.

Accordingly, there is obviously a need for a device that effectively sanitizes toothbrushes before and between uses by consumers.

There are many prior devices for sterilizing toothbrushes designed for home use. The most common method of sterilizing toothrushes employed by these devices is use of common radiant energy such as ultra-violet light to kill germs on the toothbrushes. These prior sanitizing devices include an outer housing, an ultra-violet light source located within the housing and structure within the housing to position the bristles of the brushes adjacent the light source. Proper use of these prior units may reduce the quantity of harmful bacteria found on toothbrushes.

However, these prior art devices have numerous disadvantages. Many of these prior sanitizing devices have many parts and are expensive to manufacture. In addition, many of these prior art devices are not easy to clean thoroughly and thus the sanitizing devices become a source of bacterial growth. Also, many of the prior art devices operate continuously and thus require constant replacing of the ultra-violet light bulbs. Further, some of the prior devices must be manually switched on and off, thus running the risk that toothbrushes placed therein may not be properly sterilized before the next use. Furthermore, many of the prior devices may be accidentally triggered or turned on, thus unnecessarily exposing persons to ultra-violet light. Moreover, in the prior devices having a fully enclosed housing, it may be impossible to determine if the light source is properly operating as the devices do not have an "on" indicator.

Examples of such prior toothbrush sterilizers are disclosed in U.S. Pat. No. 2,280,431 issued on Apr. 21, 1942 to Hart; U.S. Pat. No. 2,424,036 issued on July 15, 1947 to Jackel; U.S. Pat. No. 2,579,242 issued on Dec. 18, 1951 to Pask; U.S. Pat. No. 2,592,131 issued on Apr. 8, 1952 to Farrar; U.S. Pat. No. 3,100,842 issued on Aug. 13, 1963 to Tellefsen; U.S. Pat. No. 3,309,159 issued on Mar. 14, 1967 to Lesueur et al; U.S. Pat. No. 3,353,905 issued on Nov. 21, 1967 to Ellis; U.S. Pat. No. 3,748,094 issued on July 24, 1973 to Scheidell; U.S. Patent No. 3,820,251 issued on June 28, 1974 to Abernathy; U.S. Pat. No. 3,881,868 issued on May 6, 1975 to Duke; U.S. Pat. No. 3,954,407 issued on May 4, 1976 to Andary et al; U.S. Pat. No. 3,955,922 issued on May 11, 1976 to Moulthrop; U.S. Pat. No. 4,088,445 issued on May 9, 1978 to Ellis; U.S. Pat. No. 4,625,119 issued on Nov. 25, 1986 to Murdock, III; and U.S. Pat. No. 4,740,706 issued on Apr. 26, 1988 to Murdock, III; and U.S. Pat. No. 4,803,364 issued on Feb. 7, 1989 to Ritter.

Other prior radiant energy devices which are designed to sterilize items other than toothbrushes are disclosed in U.S. Pat. No. 2,554,156 issued on May 22, 1951 to Rosenthal and U.S. Pat. No. 4,698,206 issued on Oct. 6, 1987 to Nevin.

Further, a prior toothbrush and glass holder is disclosed in U.S. Pat. No. 2,336,224 issued on Dec. 7, 1943 to Cohen.

In view of the above, it is apparent that there exists a need for a toothbrush sanitizing device that can be thoroughly cleaned, minimizes the risk of accidental activation of the light source while the light source is exposed, and automatically sterilizes toothbrushes contained within the unit. This invention addresses these needs in the art, along with other needs which will become apparent to those skilled in the art once given this disclosure.

SUMMARY OF THE INVENTION

This invention provides a toothbrush sanitizing device for automatically sterilizing toothbrushes. The toothbrush sanitizer includes an outer housing having an inner surface, an inner housing having an outer surface, a cover member and a toothbrush sanitizing assembly. The inner housing is slidably received in the outer housing and is retained in the outer housing by an interference fit; The interference fit may be achieved by spaced protrusions from the outer surface of the inner housing which frictionally engage the inner surface of the outer housing. The cover member is removably supported by the inner and/or outer housings and forms an enclosure with the housings when it is on the housings. Toothbrush retaining slots are formed between the inner and outer housings. The sanitizing assembly is coupled to the inner housing and includes a sanitizing lamp positioned adjacent the toothbrush retaining slots.

In some embodiments of this invention, the cover member is shaped to also function as a drinking cup. The cover member is positioned adjacent to the sanitizing lamp so that it is sterilized at the same time the toothbrushes placed within the sanitizing devices are sterilized.

In other embodiments, the outer housing, cover member and inner housing are comprised of a heat resistant plastic, such that the cover member and the outer housing can be washed by immersion and the outer surfaces of the inner housing can be readily cleaned.

In yet other embodiments, the toothbrush retaining slots are formed by recesses in the outer surface of the inner housing and the inner surface of the outer housing. The recesses may extend longitudinally relative the unit.

In further embodiments, the inner housing includes an indicator panel which is illuminated by the sanitizing lamp when the sanitizing assembly is activated. The indicator panel is visible from the exterior of the device.

Other embodiments include centering flanges at the top of the inner housing which extend vertically. The cover member may be guided to its proper position on the housings by the centering flanges when the cover member is being placed on the housings.

In yet other embodiments, one of the centering flanges includes a switch pivotally coupled thereto which has off and on positions. The switch is biased in the off position. When the cover member is properly placed on the housings, it moves the switch from the off to the on position, activating the sanitizing assembly. The assembly has a built-in delay of a pre-determined interval such that the sanitizing lamp will not be activated for the pre-determined interval after the switch is moved to the on position and remains in the on position. Thereafter, the lamp is activated for a pre-determined time period periodically, as long as the switch remains in the on position.

The toothbrush sanitizing devices according to this invention have many advantages over prior toothbrush sanitizing devices.

One advantage of the toothbrush sanitizing devices according to this invention is that the devices may be quickly and easily disassembled for cleaning. Specifically, the inner housing can be easily removed from the outer housing. The outer housing and the cover member may be immersed in water for cleaning or washed in a dishwasher. The exterior surfaces of the inner housing can be easily washed with a wet cloth. The device can be easily reassembled after cleaning. Frequent cleaning of the device prevents the growth of bacteria in internal areas shielded from the sanitizing lamp.

Another advantage of the toothbrush sanitizing devices according to this invention is that the devices are automatically activated to sterilize toothbrushes whenever the cover is placed on the housings. Moreover, the sanitizing assembly is periodically activated when the cover member is on the housings to maintain the sanitization of the toothbrushes retained in the devices.

A further advantage of the toothbrush sanitizing devices according to this invention is that electronic circuitry of the sanitizing assembly provides a delay between the time that the switch is triggered to the time the sanitizing lamp is activated so that any accidental triggering of the switch will not activate the lamp and unnecessarily expose persons to light from the lamp.

Yet another advantage of the toothbrush sanitizing devices according to this invention is that the sanitizing lamps are only activated for short predetermined intervals during the sanitization process (when the cover is on the housings), thus maximizing the life of the sanitizing lamps.

Still another advantage of the toothbrush sanitizing devices according to this invention is that the units are relatively small and have relatively few parts, and thus are relatively inexpensive to manufacture.

Other advantages and salient features of the toothbrush sanitizing devices according to this invention will become apparent from this disclosure. An embodiment of this invention will now be described with respect to the drawings.

BRIEF DESCRIPTION OF THE DRAWINGS

Referring to the drawings which form a part of this disclosure:

FIG. 1 is a top perspective view of one embodiment of this invention with the cover member lifted above the body member and illustrating toothbrushes in place to be sanitized;

FIG. 2 is a top, exploded perspective view of the embodiment of this invention illustrated in FIG. 1;

FIG. 3 is a top view of the outer housing of the embodiment of this invention illustrated in FIGS. 1 and 2 with a support bracket secured thereto;

FIG. 4 is a longitudinal cross-sectional view, taken along section line 4—4 in FIG. 3, of the outer housing illustrated in FIGS. 1-3;

FIG. 5 is a top view of the inner and outer housings of the embodiment of this invention illustrated in FIGS. 1-4 illustrating the inner housing properly positioned within the outer housing and with the ultra-violet light assembly removed for clarity;

FIG. 6 is a longitudinal cross-sectional view, taken along section line 6—6 in FIG. 5, of the embodiment of this invention illustrated in FIGS. 1-5, with the ultraviolet light assembly removed for clarity;

FIG. 7 is a perspective view of the indicator panel of the embodiment of this invention illustrated in FIGS. 1-6;

DETAILED DESCRIPTION OF THE INVENTION

Figure 8:
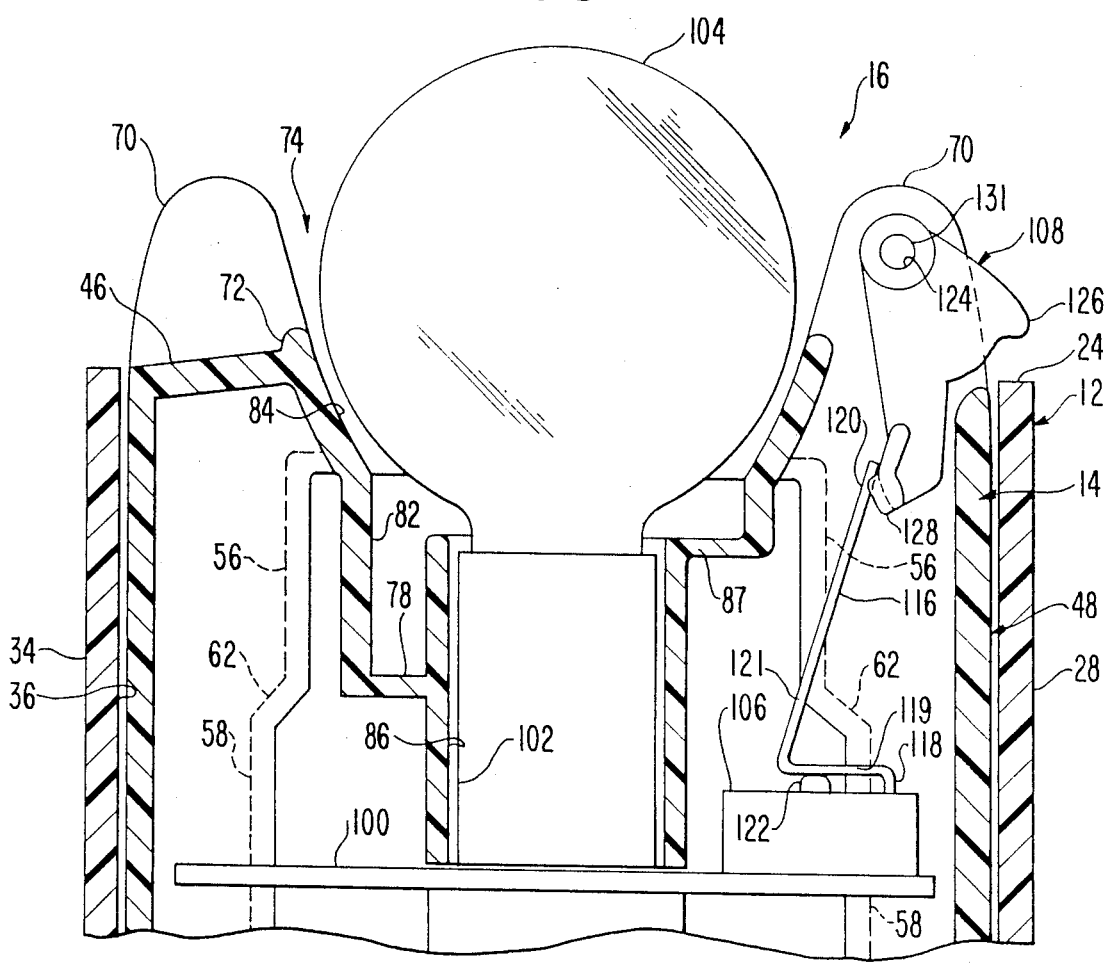
FIG. 8 is an enlarged, partial, cross-sectional view, taken along section line 8—8 in FIG. 5, of the embodiment of this invention illustrated in FIGS. 1-7, with the ultra-violet light assembly installed therein.
Figure 9:
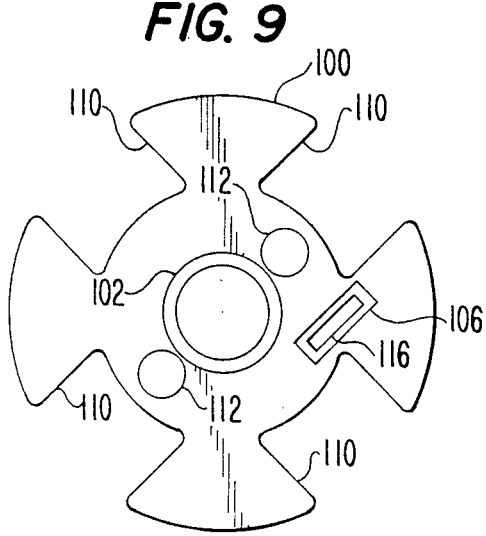
FIG. 9 is a top plan view of the electronic printed circuit board of the embodiment of this invention illustrated in FIGS. 1-8.

Referring to the Figures, and in particular FIGS. 1-3, a toothbrush sanitizing device according to this invention is illustrated, toothbrush sanitizing device 10, which includes outer housing 12, inner housing 14, ultra-violet light assembly 16, cover member 18, plug-in transformer unit 20 and mounting bracket 22. Outer housing 12, inner housing 14 and cover member 18 are preferably molded from a white plastic material such as ABS or any other suitable, non-conductive material which will not deteriorate when frequently exposed to ultra-violet light.

In the embodiment illustrated in the Figures, outer housing 12 is generally a hollow cylinder having one end closed. Outer housing 12 includes base or bottom wall 26 and cylindrical side wall 28. Base 26 and side wall 28 are integrally formed. An upper open end is defined by top rim 24 of side wall 28.

Base 26 includes outer rim portion 27 and inner concave portion 29. Rim portion 27 is flat and has four drainage openings 30 extending therethrough and three equally spaced support lugs or foot members 32 extending downwardly therefrom. In the embodiment illustrated in the Figures, drainage openings 30 are semicircles and lugs 32 are curved flanges. However, openings 30 and lugs 32 can be of any shapes which are functional.

Side wall 28 of outer housing 12 has outer surface 34, inner surface 36, cord slot 38, first mounting bracket opening 40, second mounting bracket opening 42 and cut out 44. Cord slot 38 and cut out 44 extend downward, from top rim 24, in side wall 28, cut out 44 being of a generally rectangular shape. First mounting bracket opening 40 is generally rectangular in shape. Second mounting bracket opening 42 is circular in shape, adapted to receive a portion of mounting bracket 22, as discussed below.

In the embodiment illustrated in the Figures, inner housing 14 is generally cylindrical and includes four top surfaces 46, four side surfaces 48, centering flanges 70, circular rim 72, lamp cavity 74, indicator panel 76, four recessed portions 52, protrusions 54 and drainage positioning feet 92. All of these elements are integrally formed except for indicator panel 76.

Top surfaces 46 of inner housing 14 extend from rim 72 to the periphery of inner housing 14 and are sloped slightly downwardly from rim 72 to the periphery for draining water away from light assembly 16 (discussed below). Top surfaces 46 are spaced by the upper ends of recessed portions 52, as discussed below. In the embodiment illustrated in the Figures, top surfaces 46 are substantially flat, smooth surfaces.

One of the top surfaces 46 has an indentation therein to receive indicator panel 76, as discussed below.

A centering flange 70 extends upwardly, substantially perpendicular to top surfaces 46, from one side edge of each top surface 46. The outer edges of flanges 70 slope inwardly to guide cover member 18 onto outer housing 12 when a person places cover member 18 onto housing 12 (as discussed below). One of the flanges 70 is wider than the other flanges 70, and houses lever 120 (described below).

Rim 72 surrounds lamp cavity 74 and is elevated above top surfaces 46 to prevent water from the toothbrushes properly placed within devices 10 from draining into light bulb cavity 74. Rim 72 has a gap therein which receives a portion of indicator panel 76, as discussed below.

Lamp cavity 74 includes ring base portion 78, inner cylindrical wall portion 82, spherical wall portion 84, lamp socket support member 86 and cross member 87.

Spherical wall portion 84 extends downward and inward from rim 72. Cylindrical wall portion 82 begins at the lower edge or rim of spherical wall portion 84 and extends downwardly therefrom, substantially vertical. Ring base portion 78 is at the lower edge or rim of cylindrical wall 82 and extends between cylindrical wall portion 82 and lamp socket support member 86. Lamp socket support member 86 is a cylinder which receives lamp socket 102 (described below) therein by interference fit. Cross member 87 extends between cylindrical wall portion 82 and lamp socket support member 86. Lamp socket support member 86 is approximately centered in lamp cavity 74 by ring base portion 78 and cross member 87.

Ring base portion 78 includes mounting lugs 114 which extend downward (see FIG. 6). Drainage holes 80 are formed in lugs 114 to permit water to drain from lamp cavity 74.

Outer side surfaces 48 have the same curvature and are spaced by the four recessed portions 52. Protrusions 54 protrude outwardly from side surfaces 48. Each side surface 48 has one of the protrusions 54 extending downwardly from upper surface 46. The function of protrusions 54 is discussed below. In the embodiment illustrated in the Figures, protrusions 54 are oblong shaped. In addition, one of side surfaces 48 has a slot (not shown) therein to receive the cord which extends between light assembly 16 and transformer unit 20.

Recessed portions 52 are designed to receive handles of toothbrushes therein and, in combination with outer housing 12, retain the toothbrush handles. Recessed portions 52 include upper portion 56 and lower portion 58. Portions 56 and 58 are formed by inner curved walls, substantially concentric with side surfaces 48, and side walls, which extend from the inner walls to side surfaces 48. Upper portions 56 open upwardly to upper surfaces 46 of inner housing 14 and extend downward therefrom, longitudinally relative device 10. A ledge 62 is formed at the lower end of each upper portion 56 for supporting an electric toothbrush. Lower portions 58 extend downwardly from ledges 62, also longitudinally relative device 10, to lower ledges 64. The lower ends of the handles of regular or non-electric toothbrushes are supported by lower ledges 64 when the toothbrushes are inserted into recesses 52. Ledges 62 and 64 slope outwardly towards the periphery of inner housing 14. Lower ledges 64 have drainage openings 66 at the bottom thereof for allowing water from toothbrushes retained in recessed portions 52 to drain downwardly and out of inner housing 14.

Drainage positioning feet 92 extend downwardly from lower ledges 64. Drainage openings 66 extend through drainage positioning feet 92. In the embodiment illustrated in the Figures, feet 92 are substantially semi-cylindrical in cross section. Feet 92 are sized and shaped to be received in drainage openings 30 of the outer housing 12, as shown in FIG. 5. Drainage positioning feet 92 function to align each recessed portion 52 with a drainage opening 30 so that excess water from toothbrushes placed in device 10 is rapidly and efficiently drained from unit 10.

As shown in FIG. 7, indicator panel 76 is of a generally truncated "pie piece" shape and includes upwardly extending flange 88 and fingers 90. Indicator panel 76 is comprised of a generally transparent material, to enable light to pass therethrough. Indicator panel 76 is attached to the top surface 46 having the indentation therein. Upwardly extending flange 88 is substantially in line with rim 72 (see FIGS. 1 and 2). The outer edge of indicator panel 76 and fingers 90 are received in cut-out 44 in outer housing 14.

Inner housing 14 is sized such that the four protrusions 54 frictionally engage inner surface 36 of outer housing 12 for releasably coupling inner housing 14 to outer housing 12 by an interference fit. As used herein, the phrase "interference fit" means any type of connection between outer housing 12 and inner housing 14 which allows assembly by sliding outer housing 12 and inner housing 14 together and disassembly by pulling outer housing 12 and inner housing 14 apart, while maintaining housings 12 and 14 in frictional contact. Of course, outer housing 12 and inner housing 14 may be provided with a "snap fit" connection (i.e., head and socket type) or any other quick assembly/disassembly connection.

Since outer housing 12 and inner housing 14 may be readily taken apart due to their "interference fit", unit 10 may be easily disassembled for cleaning. Further, since outer housing 12 and cover member 18 do not have any electrical parts, they may be washed in a dishwasher or by complete immersion if desired. In addition, since the exterior surfaces of inner housing 14 are comprised of a washable plastic, the exterior surfaces of inner housing 14 can be readily cleaned by a wet cloth after the unit is disassembled.

Referring to FIG. 8, ultra-violet light assembly 16 includes printed circuit board 100, light socket 102, ultra violet light bulb 104, microswitch 106 and switch assembly 108.

Printed circuit boards, such as circuit board 100, are well known in the art, and thus printed circuit board 100 and its circuitry are not illustrated or described in detail herein.

Printed circuit board 100 has a generally circular periphery with four cut outs 110 and a pair of mounting openings 112. Cutouts 110 extend inward from the periphery of circuit board 100 and are spaced approximately 90° apart. Mounting openings 112 extend through circuit board 100.

Printed circuit board 100 is mounted to the interior of inner housing 14 by fitting openings 112 around lugs 114. Mounting lugs 114 are then heated in a conventional manner, causing them to expand and engage openings 112. Cut outs 110 are received about the inner surfaces formed by recessed portions 52.

Light socket 102 is frictionally received in tubular lamp support 86 of lamp cavity 74 of inner housing 112 and threadedly receives light bulb 104 for supporting light bulb 104 in lamp cavity 74. Light socket 102 is electrically connected to printed circuit board 100 in a conventional manner. Light sockets, such as light socket 102, are well known in the art, and thus light socket 102 is not illustrated or described in detail herein.

Microswitch 106 is fixedly attached to circuit board 100. Microswitch 106 includes plunger 122 which is moveable vertically. Microswitches, such as microswitch 106, are well known in the art, and thus microswitch 106 is not illustrated or described in detail herein.

Switch assembly 108 includes contact wire 116, lever 126 and pivot pin 131. Contact wire 116 includes ends 118 and 120 and legs 119 and 121. End 118 is fixedly attached to microswitch 106. Leg 119 extends substantially horizontal from end 118 and contacts plunger 122. Leg 121 extends upward from leg 119 as shown in FIG. 8. End 120 is the free end of leg 121 and contacts lever 126.

Lever 126 is basically a flat plate having leg receiving member 128. Leg receiving member 128 is of a greater thickness than the plate formed by lever 126 and includes a recessed portion to receive end 120 of contact wire 116.

Lever 126 is pivotably mounted in one of the centering flanges 70. The centering flange 70 having lever 126 mounted therein has a pair of axially aligned bores for receiving pivot pin 131 therein. Lever 126 is mounted on pivot pin 131 to pivotably couple lever 126 to centering flange 70.

Leg receiving member 128 of lever 126 engages free end 120 of contact lever 116, which biases lever 126 in a counter-clockwise direction around pivot pin 131, as illustrated in FIG. 8. Accordingly, a portion of lever 126 extends outwardly beyond centering flange 70, for engaging cover member 18 as discussed below.

Cover member 18 is a hollow cylinder having one end closed. Cover member 18 has approximately the same outer diameter as outer housing 12.

Cover member 18 also may function as a cup, which is simultaneously sanitized with the toothbrushes in device 10 by the ultra-violet light from light bulb 104.

Transformers, such as plug-in transformer unit 20, are well known in the art, and thus transformer 20 is not illustrated or described in detail herein.

Plug-in transformer unit 20 reduces the voltage available from a standard wall electrical outlet to a lower voltage for operating toothbrush sanitizer 10. Electrical cord 124 extends from the plug-in transformer unit 20 through cord slot 30 to the printed circuit board 100 in a conventional manner.

Figure 10:
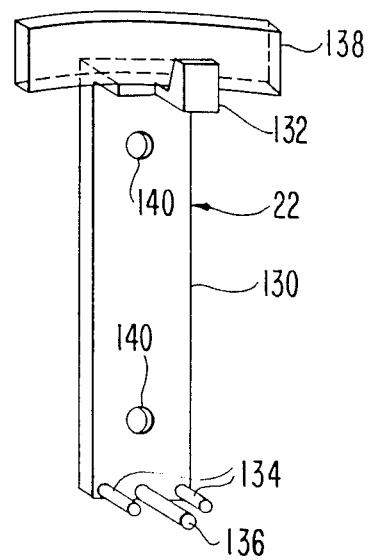
FIG. 10 is a right perspective view of the mounting bracket of the embodiment of this invention illustrated in FIGS. 1-9.

Toothbrush sanitizing device 10 can be mounted to a wall by using mounting bracket 22 (see FIG. 10). Mounting bracket 22 includes L-shaped body portion 130, hook member 132, a pair of stabilizing pegs 134, positioning peg 136, and curved stabilizing member 138.

Body portion 130 has a pair of mounting holes 140 for receiving fasteners, such as screws, for mounting the bracket 22 to a wall or the like. When using mounting bracket 22 to mount toothbrush sanitizing device 10 to a wall, hook member 136 is received in first mounting bracket opening 40 while positioning peg 136 is received in second mounting opening 42 as shown in FIG. 4. Stabilizing pegs 134 and curved stabilizing member 138 abut outer housing 12 to prevent toothbrush sanitizer unit 10 from moving relative to mounting bracket 22.

Toothbrush sanitizing device is assembled as discussed above and used as follows. When a consumer has a toothbrush to be sanitized, the consumer lifts cover member 18 off of outer housing 14 and inserts the handle of the toothbrush into a recess 52, with the bristles of the toothbrush facing light bulb 104. The consumer then repositions cover member 18 on outer housing 14. During this repositioning, cover member 18 may engage flanges 70 and flanges 70 may guide cover member 18 into the proper position on outer housing 14.

Also, when cover member 18 is re-positioned on outer housing 14, cover member 18 engages lever 126, pivoting lever 126 clockwise (as shown in FIG. 8) around pivot pin 131. This pivoting movement causes wire engaging portion 128 to push on leg 121 of contact wire 116, rotating wire 116 counter-clockwise about end 118 since end 118 is affixed to microswitch 106. This rotational movement causes leg 119 to push down on plunger 122, activating microswitch 106.

The circuitry of circuit board 100 has a built-in time delay such that the actual activation of light assembly 16 is delayed for a short, predetermined period of time after microswitch 106 is actuated and remains actuated. This time delay prevents accidental actuation of ultra-violet light bulb 104 when cover member 18 is not in place and prevents actuation if cover member 18 is placed onto housing 14 but immediately removed. For example, light bulb 104 will not be turned on if lever 126 is accidentally bumped and temporarily rotated when cover member 18 is off of outer housing 12.

The circuitry of circuit board 100 is also designed to periodically actuate light bulb 104 (for example, for approximately two minutes every ½ hour that microswitch 106 is continuously actuated), to provide continual sanitization of the toothbrushes in device 10.

When ultra-violet light bulb 104 is actuated, light from bulb 104 will be transmitted through indicator panel 76 to its outer portion 90 to indicate that device 10 is sterilizing toothbrushes contained in device 10.

Since lever 126 is biased to the "off" position as discussed above, lever 126 will move to the "off" position whenever cover member 18 is removed. Thus, whenever cover member 18 is removed, microswitch 106 is deactivated and light bulb 104 is turned off.

If excessively wet toothbrushes are inserted into device 10, the excess water on the toothbrushes will drain out through drainage openings 66 or 80. Specifically, if the excess water drains down the handles of the toothbrushes or down recessed portions 52, the water will drain out of device 10 through openings 66. If the excess water drips off of the bristles of the toothbrush(es) into lamp cavity 74, the water will run down wall portions 82 and 84 onto base ring portion 78. The water will then drain through drainage holes 80 in lugs 114 onto the center portion of base 26 of outer housing 14. Since the center portion of base 26 is inner concave portion 29, the water will be directed out drainage openings 30, it being noted that there is space provided between feet 92 and the walls of openings 30 to permit this excess water to drain out of device 10 through that space.

Various modifications, improvements and other embodiments will become apparent to those skilled in the art once given this disclosure. Such modifications, improvements and other embodiments are considered to be within the scope of this invention as defined by the following claims.

What is claimed is:

1. A toothbrush sanitizing device comprising:
   a base member including an outer housing having an inner surface and an inner housing having an outer surface, said inner housing being removably received within said outer housing;
   a cover member removably supported by of said base member, said cover member and said outer housing forming an enclosure when said cover member is supported by said base member;
   means formed by said outer and inner housings for retaining at least one toothbrush within said enclosure; and
   an ultraviolet lamp assembly for sanitizing toothbrushes retained in said retaining means, said ultraviolet lamp assembly being coupled to said inner housing and including a lamp positioned adjacent the bristles of the toothbrushes retained in said retaining means;
   wherein said outer housing and said outer surface of said inner housing include coupling means for removably retaining said inner housing within said outer housing by an interference fit.

2. A toothbrush sanitizing device according to claim 1, wherein
   said outer housing has a bottom surface and a continuous side wall,
   said bottom surface having drainage holes therethrough.

3. A toothbrush sanitizing device according to claim 2, wherein
   said side wall has an upper rim, said upper rim supports said cover member when said cover member is placed on said outer housing.

4. A toothbrush sanitizing device according to claim 1 wherein
   said cover member is of a shape and size such that it can be employed as a drinking cup.

5. A toothbrush sanitizing device according to claim 1 wherein
   said retaining means is formed by 1) recesses in the outer surface of said inner housing and 2) said inner surface of said outer housing, said recesses extending longitudinally.

6. A toothbrush sanitizing device according to claim 5 wherein
   said outer housing has a bottom surface and a continuous side wall, said bottom surface having drainage holes therethrough,
   said recesses having openings at the bottom thereof which are in alignment with said drainage holes.

7. A toothbrush sanitizing device according to claim 1, wherein
   said coupling means includes at least one protrusion extending outwardly from said outer surface of said inner housing to frictionally engage said inner surface of said outer housing.

8. A toothbrush sanitizing device according to claim 7, wherein,
   said inner housing has an upper surface;
   said protrusion is generally oblong shaped and extends downwardly from said upper surface of said inner housing.

9. A toothbrush sanitizing device according to claim 8, wherein
   said coupling means includes a plurality said protrusions for frictionally engaging said inner surface of said outer housing.

10. A toothbrush sanitizing device according to claim 9, wherein
    said inner housing includes an indicator panel that is illuminated by light from said lamp, said indicator panel extending to the exterior of said device.

11. A toothbrush sanitizing device according to claim 1, wherein
    said inner housing includes centering means extending upward at the top of said inner housing for positioning said cover member on said base member, said centering means comprising a plurality of spaced, vertical flanges.

12. A toothbrush sanitizing device according to claim 11, wherein
    said lamp assembly has an automatic delay of a pre-determined interval when said switch is moved from the off to the on position such that said lamp will not be activated for said pre-determined interval after said switch is moved from off to the on position and remains in said position.

13. A toothbrush sanitizing device according to claim 1, wherein
    one of said flanges has a pivotably mounted switch coupled thereto which is connected to said lamp assembly and functions to activate and deactivate the lamp assembly.

14. A toothbrush sanitizing device according to claim 13, wherein
    said switch has off and on positions, said switch being biased in the off position, said switch being moved from said off position to said on position when said cover member is placed on said outer and inner housings.

15. A toothbrush sanitizing device according to claim 1, wherein
    said lamp is automatically activated for a pre-determined time period periodically when said switch is in the on position.

16. A toothbrush sanitizing device comprising a housing including means for retaining at least one toothbrush;

a cover member removably supported by said housing, said cover member and said housing forming an enclosure when said cover member is being supported by said housing, said enclosure containing toothbrushes retained in said retaining means; and means for sanitizing toothbrushes attached to said housing and including an ultraviolet lamp assembly;

said sanitizing means including a switch rotatably affixed to said housing and having on and off positions, said switch being biased in the off position;

wherein when said cover member is placed on said housing, said cover member moves said switch from the off position to the on position;

said sanitizing means having an automatic delay of a pre-determined interval such that said lamp is not activated when said switch is moved from the off position to the on position until said switch remains in the on position for said pre-determined interval.

17. A toothbrush sanitizing device comprising:

an outer housing having a side wall structure with an outer surface and an inner surface, a substantially closed end and an open end, said closed end having at least one drainage opening therein;

an inner housing having an upper surface with centering means and an outer peripheral surface with at least one recess therein for selectively receiving a toothbrush, said recess being aligned with said drainage opening so that water from the toothbrush can flow down said recess and out of said outer housing through said drainage opening;

a cover member removably mounted on said housings about said centering means for completely enclosing the toothbrush within an enclosure formed by said outer housing and said cover member when said cover member is received on said housings;

an ultraviolet lamp assembly coupled to said inner housing for sterilizing the toothbrush contained within said outer housing and said cover member; and coupling means, associated with said inner surface of said side wall structure and said peripheral surface of said inner housing, for removably retaining said inner housing within said outer housing by an interference fit between said inner and outer housings.

18. A toothbrush sanitizing device comprising:

a base member including an outer housing and an inner housing, said inner housing being removably received within said outer housing;

a cover member removably supported by said base member, said cover member and said base member forming an enclosure when said cover member is supported by said base member;

means formed by said outer and inner housings for retaining at least one toothbrush within said enclosure such that said toothbrush is completely enclosed within said enclosure, said retaining means being accessible only when said cover member is removed from said base member; and an ultraviolet lamp assembly for sanitizing toothbrushes retained in said retaining means, said ultraviolet lamp assembly being coupled to said inner housing.

19. A toothbrush sanitizing device comprising:

a base member including an outer housing and an inner housing, said inner housing being removably received within said outer housing;

a cover member removably supported by said base member, said cover member and said base member forming an enclosure when said cover member is supported by said base member;

means formed by said outer and inner housings for retaining at least one toothbrush within said enclosure; and means for sanitizing toothbrushes retained in said retaining means, said sanitizing means being coupled to said inner housing and including an ultraviolet lamp assembly;

said sanitizing means including a switch rotatably affixed to said housing and having on and off positions, said switch being biased in the off position;

wherein when said cover member is placed on said base member, said cover member moves said switch from the off position to the on position;

said sanitizing means having an automatic delay of a pre-determined interval such that the lamp of said lamp assembly is not activated when said switch is moved from the off position to the on position until said switch remains in the on position for said pre-determined interval.

* * * * *